(12) United States Patent
Stonebridge et al.

(10) Patent No.: US 9,067,026 B2
(45) Date of Patent: Jun. 30, 2015

(54) VASCULAR GRAFT

(75) Inventors: Peter Arno Stonebridge, Perth (GB); John Bruce Cameron Dick, Coupar Angus Blairgowrie (GB); John Graeme Houston, Perth Tayside (GB); Robert Gordon Hood, Longforgan Tayside (GB)

(73) Assignee: Vascular Flow Technologies Limited (GB)

( * ) Notice: Subject to any disclaimer, the term of this patent is extended or adjusted under 35 U.S.C. 154(b) by 0 days.

(21) Appl. No.: 13/320,966

(22) PCT Filed: May 19, 2010

(86) PCT No.: PCT/GB2010/001015
§ 371 (c)(1),
(2), (4) Date: Feb. 9, 2012

(87) PCT Pub. No.: WO2010/133848
PCT Pub. Date: Nov. 25, 2010

(65) Prior Publication Data
US 2012/0130314 A1 May 24, 2012

(30) Foreign Application Priority Data

May 19, 2009 (GB) .................................. 0908614.1
Feb. 26, 2010 (GB) .................................. 1003334.8

(51) Int. Cl.
*A61M 5/00* (2006.01)
*A61M 1/36* (2006.01)
(Continued)

(52) U.S. Cl.
CPC ................. *A61M 1/3655* (2013.01); *A61F 2/88* (2013.01); *A61F 2/06* (2013.01); *A61M 39/0208* (2013.01);
(Continued)

(58) Field of Classification Search
CPC ............... A61F 2/06; A61F 2/07; A61F 2/88;
A61F 2002/068; A61M 1/3655; A61M 1/3653; A61M 39/0208; A61M 2206/12; A61B 17/11; A61B 2017/1107; F15D 1/065; B29C 45/14622
USPC ............................... 604/8, 9, 86, 175; 28/143
See application file for complete search history.

(56) References Cited

U.S. PATENT DOCUMENTS 4,619,641 A   10/1986 Schanzer
5,716,395 A *  2/1998 Myers et al. .................... 623/1.5
(Continued)

FOREIGN PATENT DOCUMENTS

EP   1759667 A1   3/2007
EP   1886705 A1   2/2008
(Continued)

OTHER PUBLICATIONS

Kaden, Malte, "PCT Application No. PCT/GB2010/001015 International Preliminary Report on Patentability Dec. 1, 2011", , Publisher: PCT, Published in: PCT.
(Continued)

*Primary Examiner* — Tatyana Zalukaeva
*Assistant Examiner* — Andrew J Mensh
(74) *Attorney, Agent, or Firm* — Kaplan Breyer Schwarz & Ottesen, LLP

(57) ABSTRACT

A vascular access graft (1) comprises an elongate conduit (2) having proximal and distal ends (3, 4). At least a portion of the elongate conduit (2) has a self-sealing property such that the portion remains impermeable after puncturing by a dialysis needle. The vascular access graft (1) also comprises a helical fin (6) projecting inwardly from the inner surface (5) of the elongate conduit (2) and extending parallel to the axis of the elongate conduit (2).

19 Claims, 3 Drawing Sheets

(51) Int. Cl.
| | | |
|---|---|---|
| A61M 37/00 | (2006.01) | |
| A61M 5/32 | (2006.01) | |
| A61F 2/06 | (2013.01) | |
| A61F 2/88 | (2006.01) | |
| A61M 39/02 | (2006.01) | |
| F15D 1/06 | (2006.01) | |
| A61B 17/11 | (2006.01) | |
| A61F 2/07 | (2013.01) | |
| B29C 45/14 | (2006.01) | |

(52) U.S. Cl.
  CPC ............ *A61M 2206/12* (2013.01); *F15D 1/065* (2013.01); *A61B 17/11* (2013.01); *A61F 2/07* (2013.01); *B29C 45/14622* (2013.01); *A61B 2017/1107* (2013.01); *A61M 1/3653* (2013.01); *A61F 2002/068* (2013.01); *A61M 2206/16* (2013.01)

(56) References Cited

U.S. PATENT DOCUMENTS

| | | | |
|---|---|---|---|
| 5,849,036 | A | 12/1998 | Zarate |
| 6,261,257 | B1 | 7/2001 | Uflacker et al. |
| 6,585,762 | B1 | 7/2003 | Stanish |
| 7,108,673 | B1 | 9/2006 | Batiste |
| 7,563,247 | B2 * | 7/2009 | Maguire et al. ............... 604/104 |
| 2012/0059305 | A1 * | 3/2012 | Akingba ........................... 604/9 |

FOREIGN PATENT DOCUMENTS

| | | |
|---|---|---|
| GB | 2369797 A | 6/2002 |
| GB | 2429650 A | 3/2007 |
| WO | 8906566 A1 | 7/1989 |
| WO | 9724081 A1 | 7/1997 |
| WO | 0038591 A2 | 7/2000 |
| WO | 0128456 A1 | 4/2001 |
| WO | 03045379 A1 | 6/2003 |
| WO | 2004047908 A2 | 6/2004 |
| WO | 2005004751 A1 | 1/2005 |
| WO | 2005077305 A1 | 8/2005 |
| WO | 2005092240 A1 | 10/2005 |
| WO | 2006026725 A2 | 3/2006 |
| WO | 2007061787 A2 | 5/2007 |

OTHER PUBLICATIONS

"Related Japanese Patent Application No. 2012-511340 Office Action", Jan. 20, 2014, Publisher: JPO, Published in: JP.
Daugirdas, et al. "Handbook of Dialysis.", dated Dec. 8, 2006.
Written Opinion of International Application No. PCT/GB2010/001015, dated May 19, 2010.
Search Report of GB0908614.1, dated Aug. 28, 2009.
Hazinedaroglu, et al., "Transplantation Proceedings" 2004; pp. 2599-2602.
Wearn, et al., "Asian Cardiovascular and Thoracic Annals" 2003; pp. 314-318.
Zheng, et al., "American Society for Artificial Internal Organs" 2009; pp. 192-199.

* cited by examiner

VASCULAR GRAFT

FIELD OF THE INVENTION

The present invention relates to a vascular access graft, in particular, a vascular access graft of the type that is self-sealing upon being punctured.

BACKGROUND OF THE INVENTION

Individuals suffering from kidney failure require regular blood dialysis treatment. Such dialysis treatment requires the removal of blood from the individual and the cycling of the blood through a dialysis machine that performs the function of the failed kidney. After processing, the blood is then returned to the individual. Typically, the procedure is performed three times a week over many years and each treatment requires the insertion of a dialysis needle for withdrawal and returning of the blood. Furthermore, dialysis requires a relatively rapid blood flow rate so it is necessary for the dialysis needles to be quite large.

The problem with regular dialysis treatment of this type is that the natural blood vessels of patients are of insufficient strength to withstand collapse from frequent puncturing with large bore needles and allow sufficient flow rate through the vessel to achieve an acceptable rate of dialysis. One solution to this problem is to create a site within a patient, in a surgical procedure, by bridging an artery and a vein under the skin on the inside of the forearm or the upper thigh with a synthetic graft. This surgical procedure provides an easily accessible blood vessel into which the dialysis needles are inserted. It is instead possible to form an autograft by suturing together an artery and a vein but, while this creates an easily accessible site, the auto graft is still susceptible to scarring and collapse as with any natural blood vessels.

Where a synthetic graft (which will hereinafter be termed an "access graft" or "shunt grant") is implanted, it is desirable that the graft has self-sealing properties because otherwise blood can leak from apertures left in the access graft following puncturing by the dialysis needles, particularly in the weeks immediately following implantation of the access graft and prior to full healing around the graft (see Daugirdas et al Handbook of Dialysis).

Many different types of access grafts with self-sealing properties are known in the art. For example, in U.S. Pat. No. 4,619,641 there is disclosed an access graft which comprises a coaxial double lumen tube. The inner and outer tubes are made from, for example, Teflon PTFE or Dacron synthetic polyester fibre. The space between the outer tube and the inner tube is filled with a biocompatible polymer such as silicone rubber sealant.

WO01/28456 discloses a laminated self-sealing vascular access graft. The graft comprises an inner layer, an intermediate layer concentrically surrounding the inner layer and an outer layer concentrically surrounding both the inner and intermediate layers. The inner layer is made from expanded PTFE. The intermediate layer comprises alternating regions of materials of different densities, including a low density material such as PTFE "cotton".

Other examples of self-sealing access grafts include grafts composed of heparin-bonded polycarbonate (see Hazinedaroglu et al Transplantation Proceedings 2004; 36(9): 2599 to 2602) or polyurethane (see Wearn et al Asian Cardiovascular and Thoracic Annals 2003; 11: 314-318).

The problem with such synthetic access grafts is that at the artery/vein junction, the internal lumen of the graft can narrow over time. Furthermore, repeated puncturing of even synthetic, self-sealing access grafts during the dialysis process can result in internal scarring which leads to reduced flow and eventual occlusion. Moreover, blood flowing through an access graft is generally very turbulent especially when a dialysis needle is inserted into the graft, during dialysis. The turbulent flow results in fibrils forming on the interior of the access grafts, again leading to reduced flow and even occlusion of the access graft.

The present invention seeks to alleviate one or more of the above problems.

SUMMARY OF THE INVENTION

According to the present invention, there is provided a vascular access graft comprising an elongate conduit having distal and proximal ends, at least a portion of the elongate conduit having a self-sealing property such that the portion remains impermeable after puncturing by a dialysis needle, wherein the vascular access graft further comprises a helical fin projecting inwardly from the inner surface of the elongate conduit and extending parallel to the axis of the elongate conduit.

Conveniently, the helical fin extends from the distal end of the elongate conduit to a termination point which is short of the proximal end of the elongate conduit.

Preferably, the helical fin extends from the distal end of the elongate conduit for less than 50% of the total length of the elongate conduit, more preferably less than 25% thereof, more preferably less than 15% thereof.

Advantageously, the helical fin has a helix angle of between 5° and 20°, preferably between 8° and 17°, most preferably between 8° and 16°.

Conveniently, the helix angle of the helical fin changes over the length of the helical fin.

Preferably, the helical fin consists of between 50% and 150% of one single revolution, more preferably between 80% and 120% of one single revolution.

Conveniently, the helical fin projects inwardly from the inner surface of the elongate conduit to a position between 35% and 65% of the distance from the inner surface to the longitudinal axis of the elongate conduit, preferably between 40% and 60% of the distance, more preferably between 45% and 55% and most preferably 50% of the distance.

Advantageously, the vascular access graft further comprises an external palpable protrusion on the exterior of the elongate conduit, wherein the positioning of the protrusion on the conduit corresponds to the position of the termination point of the helical fin between the distal and proximal ends of the elongate conduit.

Preferably, the palpable protrusion is a palpable ring which completely or partially encircles the exterior of the elongate conduit.

Preferably, the palpable protrusion extends between 1 mm and 4 mm from the exterior of the elongate conduit, more preferably 2 mm from the exterior of the elongate conduit.

Advantageously, the palpable protrusion has a length of between 3 mm and 6 mm along the length of the elongate conduit, preferably between 4 mm and 5 mm, and most preferably has a length of 4.5 mm along the length of the elongate conduit.

Conveniently, the vascular access graft further comprises an external helical formation extending axially around the exterior of the elongate conduit, for supporting the elongate conduit.

Preferably, the helix angle of the external helical formation is greater than the helix angle of the helical fin.

Advantageously, the external helical formation has a helix angle of greater then 50°, preferably between 65° and 80°.

Conveniently, the distal and and/or the proximal end of the elongate conduit comprise an anastomosis hood. The anastomosis hood facilitates the attachment of the vascular access graft to a vein or artery.

Preferably, the vascular access further comprises an axially extending external deformation helix located around the outside of the elongate conduit, wherein the deformation helix deforms the elongate conduit so as to provide the helical fin projecting inwardly from the inner surface of the elongate conduit such that the internal helical fin corresponds to the external deformation helix, and wherein the palpable protrusion is an integral part of the deformation helix. The deformation helix and the palpable protrusion are made by the method described in WO 2005/092240, which is herein incorporated by reference.

Alternatively, the palpable protrusion is separate from the deformation helix and is secured to the exterior of the elongate conduit. For example, the palpable ring is clamped around the elongate conduit.

Advantageously, the elongate conduit is made from ePTFE, and the deformation helix and the palpable ring are made from a non-deformable material such as polyurethane.

The helical fin imparts helical flow on blood passing through the vascular access graft.

The terms "helix" and "helical" are used herein to cover the mathematical definitions of helix and helical and any combination of mathematical definitions of helical and spiral.

A "helix angle" referred to herein is the angle between the helix and the axial line about which it is formed, in particular the axis of the tubular graft.

Figure 6:
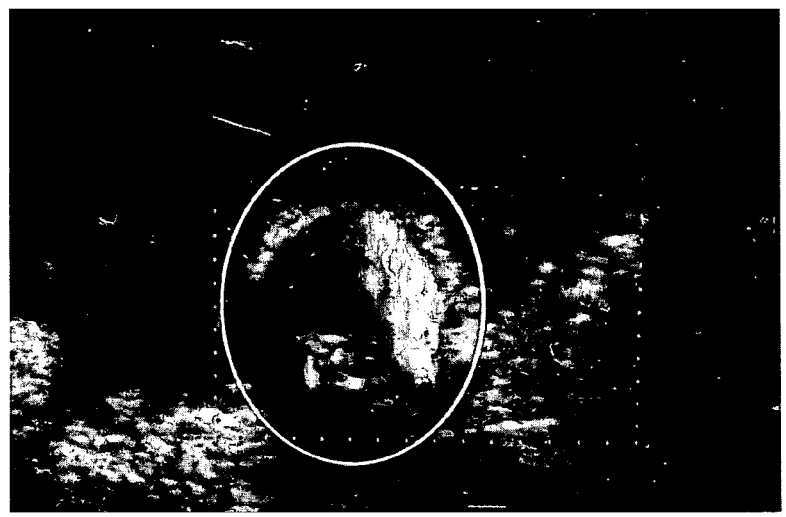
FIG. 6 is an ultra-sound image demonstrating spiral laminar flow at the distal anastomosis of a vascular access graft. The light grey/dark grey colour split which is circled in the image indicates the rotatory component of blood flow around the arterial axis, as is found in healthy arteries and in the vascular access graft.
Figure 7:
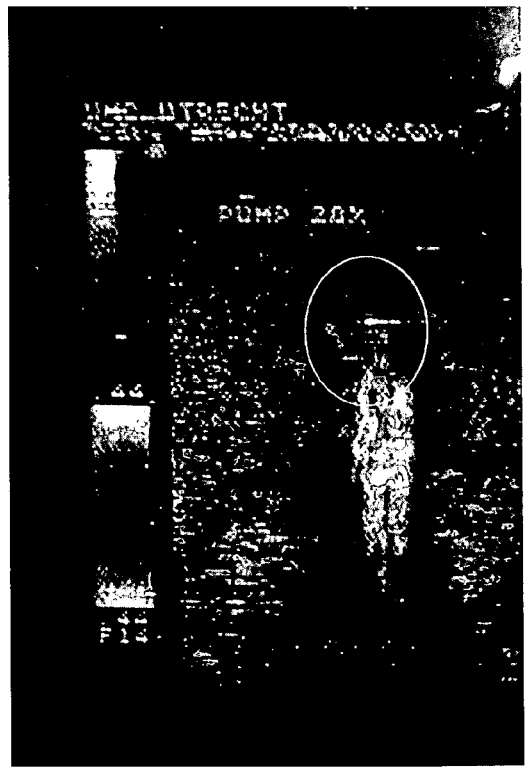
FIG. 7 is an ultra-sound image showing spiral laminar flow at the distal anastomosis of a vascular access graft during extra corporeal blood pumping simulating in-vivo dialysis conditions. The circled area on FIG. 7 shows that the light grey/dark grey colour split is present, therefore spiral laminar flow is present.

The images of FIGS. 6 and 7 were obtained using ultrasound imaging techniques during an animal study in September 2009.

DETAILED DESCRIPTION

Figure 1:
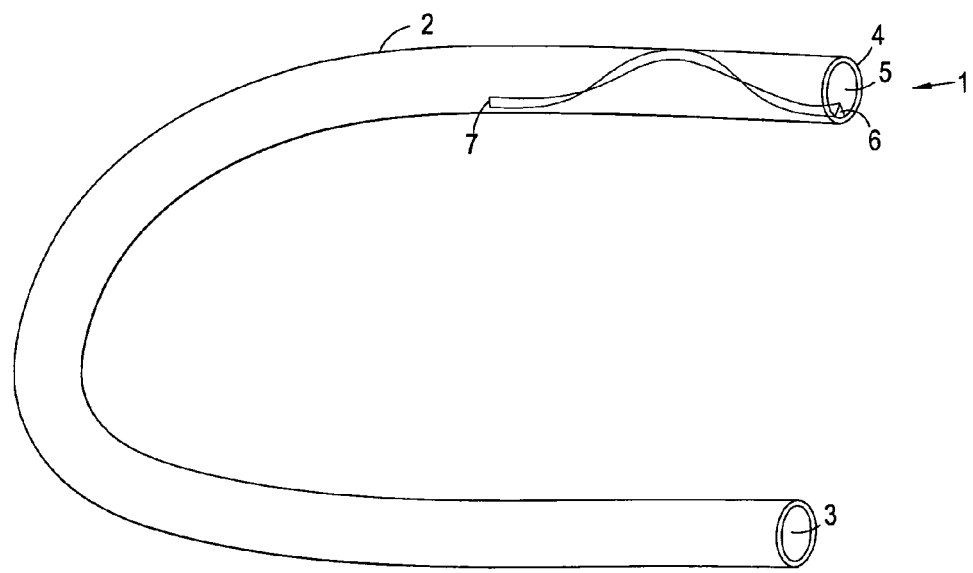
FIG. 1 is a perspective view of a vascular access graft, in accordance with one embodiment of the present invention, with some hidden detail shown.

Referring to FIG. 1, a vascular access or shunt graft 1 comprises an elongate conduit 2 which has self-sealing properties. The elongate conduit 2 is made from a flexible material. In this embodiment, the elongate conduit 2 comprises an inner tube located coaxially within an outer tube, wherein the inner and outer tubes are made from ePTFE. The space between the inner and outer tubes is filled with a self-sealing, non-biodegradable, biocompatible polymer such as a silicone rubber sealant as described in U.S. Pat. No. 4,619,641 which is incorporated herein by reference.

However, it is not essential to the present invention that the self-sealing properties of the elongate conduit 2 are conferred by this manner of construction. Therefore, in alternative embodiments, the elongate conduit 2 is made from a heparin-bonded polycarbonate/urethane as described in Hazinedaroglu et al, Transplantation Proceedings 2004; 36(9): 2599 to 2602, which is incorporated herein by reference. Alternatively, the access graft may be a polyurethane graft such as is described in Wearn et al., Asian Cardiovascular and Thoracic Annals 2003: 11: 314-318 or a multi layer access graft as described in WO01/28456, each of which is also incorporated herein by reference. What is important is that following the puncturing of the wall of the elongate conduit 2 by a dialysis needle (that is to say after insertion and removal of the dialysis needle) the wall of the elongate conduit 2 remains impermeable such that, when implanted, blood is not released from the vascular access graft 1, after puncturing.

The elongate conduit 2 comprises proximal and distal ends 3, 4 which are in fluid communication with each other via the internal lumen of the elongate conduit 2 which is defined by the inner surface 5 of the elongate conduit 2. A helical fin 6 projects inwardly from the inner surface 5 of the elongate conduit 2 and extends parallel to the axis of the elongate conduit 2 from the distal end 4 of the elongate conduit 2 to a termination point 7 such that the helical fin 6 consists of one single revolution. That is to say, the helical fin 6 makes one complete turn of 360°. As shown in Example 1 herein, only a single revolution of an internal helical fin is required in order to impart helical flow on blood passing through the conduit 2. In alternative embodiments, the helical fin may be longer or shorter than this and may, for example, be between 50% and 150% of a single revolution, preferably between 80% and 120% thereof.

In this embodiment, the cross section of the helical fin 6 is of a bell shape. However, in alternative embodiments, the helical fin has a different cross section such as having a U-shaped cross-section as is described in WO03/045379 or a triangular cross section such as described in WO2005/004751, each of which are incorporated herein by reference.

The height of the helical fin 6 (that is to say the distance from the inner surface 5 of the elongate conduit 2 to the tip of the helical fin 6) is 50% of the radius the elongate conduit 2. The radius of the elongate conduit 2 is the distance from the inner surface 5 of the elongate conduit 2 to the longitudinal axis of the elongate conduit 2. A helical fin 6 of this height produces the optimal spiral flow pattern of blood passing through the conduit. However, in alternative embodiments, the height of the helical fin 6 may be between 35% and 65%, 40% and 60% or 45% and 55% of the radius of the elongate conduit.

It is to be appreciated that the helical fin 6 extends for only a part of the length of the elongate conduit 2. The total length of the elongate conduit 2 (i.e. the distance from the proximal end 3 to the distal end 4) varies from patient to patient and depends upon the site of implantation but is typically between 30 and 50 cm. While the proportion of the length of the elongate conduit 2 which bears the helical fin 6 also varies from patient to patient, the portion of the elongate conduit 2 that bears the helical fin 6 is generally less than 50% of the total length of the elongate conduit. In preferred embodiments, less than 25% or less than 15% of the total length of the elongate conduit 2 bears the helical fin 6. It is preferred to minimise the length of the elongate conduit 2 which bears the helical fin 6 since, if, during an attempted insertion of a dialysis needle, the needle impinges upon the helical fin 6 then the helical fin 6 will generally prevent the insertion of the dialysis needle.

Figure 3:
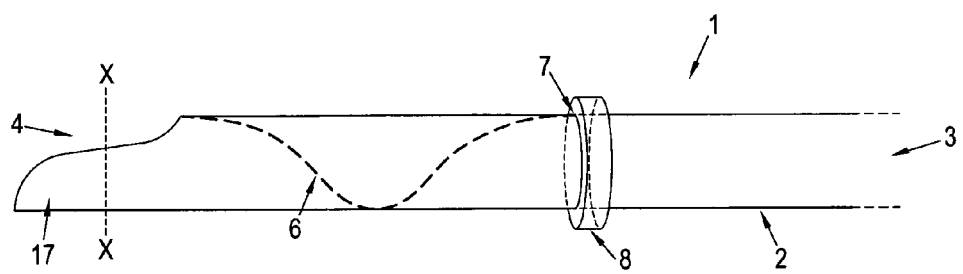
FIG. 3 is a side view of a portion of a vascular access graft comprising an external palpable ring, in accordance with one embodiment of the invention.

FIG. 3 shows an embodiment wherein there is a non-deformable palpable ring 8 encircling the elongate conduit 2. The location of the palpable ring 8 around the exterior of the conduit 2 corresponds to the position of the termination point 7 of the helical fin 6 between the distal and proximal ends 3, 4, of the elongate conduit 2. This indication of the termination point 7 of the helical fin 6 is useful to prevent accidental insertion of a dialysis needle into the helical fin 6 as described above. The palpable ring 8 protrudes radially uniformly outwardly by 2 mm from the exterior of the elongate conduit 2 and extends for 4.5 mm along the length of the conduit 2. In preferred embodiments of the present invention the vascular access graft 1 further comprises an anastomosis hood 17 at the distal end 4 of the conduit 2. The anastomosis hood 17 is an ePTFE flap which extends beyond the distal end 4 of the elongate conduit 2. The hood 17 has a tubular shape equivalent to that of the elongate conduit 2, wherein part of the tube is cut-away. From a side view, as shown in FIG. 3, the cutaway edge of the hood 17 is S-shaped. The hood 17 has a U-shaped cross-section along the line x-x. The helical fin 6 is initiated at a position opposite the anastomosis hood 17. An anastomosis hood is also provided at the proximal end 3 of the conduit (not shown in FIG. 3).

The helix angle of the helical fin 6 is between 5° and 20°, preferably between 8° and 16°. The higher the helix angle, the shorter the helical fin 6 is required to be (that is to say the closer the termination point 7 is to the distal end 4 of the elongate conduit 2) while completing a single revolution. In some embodiments, the helix angle of the helical fin 6 changes over the length of the fin. For example, in one embodiment the helix angle of the helical fin is 5° at the termination point 7 and the helix angle steadily increases such that it is 16° at the distal end 4 of the elongate conduit 2. In one embodiment, there are provided two or three helical fins 6 extending from the distal end 4 of the conduit 2.

In some embodiments, an external helical formation for supporting the elongate conduit 2 is provided around the elongate conduit 2. The external helical formation (not shown) has a higher helix angle than the helical fin 6. The helix angle of the external helical formation is generally greater than 50°, and preferably between 65° and 80°. Further details of a suitable external helical formation and of details of how a graft may be provided with an internal helical fin and optionally an external helical formation are disclosed in WO2005/092240, which is incorporated herein by reference. Such an external helical formation prevents kinking of the elongate conduit 2. However, since the elongate conduit 2 is self-sealing and comprises axial tubing with a self-sealing biocompatible polymer between the inner or outer tubes, kinking of the elongate conduit 2 is not generally problematic. Therefore the external helical formation can be omitted which has the advantage that the external helical formation does not interfere with the insertion of dialysis needles into the elongate conduit 2.

Figure 4:
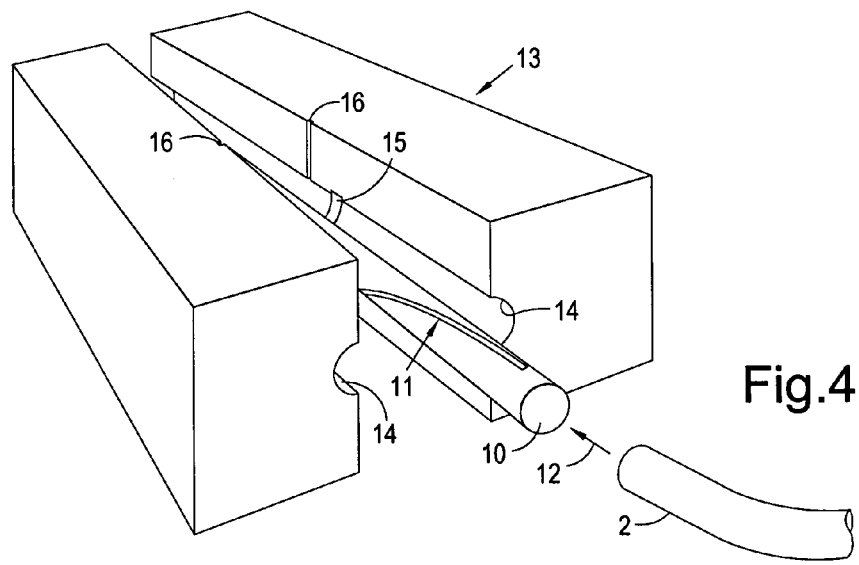
FIG. 4 is a perspective view of a vascular access graft prior to insertion in the moulding equipment used to arrive at one embodiment of the vascular access graft of the present invention.
Figure 5:
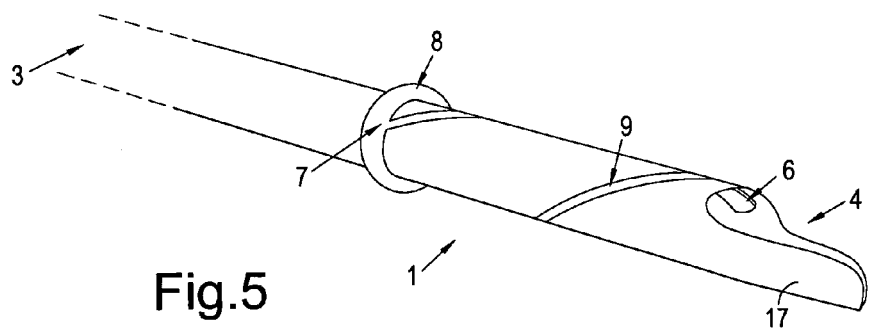
FIG. 5 is a perspective view of a portion of a vascular access graft in accordance with one embodiment of the present invention.

FIG. 5 shows an embodiments of the present invention wherein the vascular graft 1 further comprises an axially extending external deformation helix 9, wherein the palpable protrusion 8 is an integral part of the deformation helix 9. The helical fin 6 is formed by the method described in WO 2005/092240. The method is herein incorporated by reference. The formation of the palpable ring 8 is achieved simultaneously using this method, to give an integrally linked deformation helix 9 and palpable ring 8. FIG. 4 shows moulding apparatus suitable for use with this method, wherein the elongate conduit 2 is placed on a cylindrical mandrel 10 in the direction of the arrow 12. The mandrel 10 has an axially extending helical channel 11 on its surface. The size and length of the channel 11 correspond to the desired dimensions of the helical fin 6 of the graft 1. The elongate conduit 2 and mandrel 10 are tightly encased within a mould 13. The inner surfaces 14 of the mould 13 encasing the conduit 2 and mandrel 10 form a cylinder and the cylinder has an axially extending ring-shaped channel 15 in its surface (corresponding to the palpable ring 8). Molten polyurethane is injected between the conduit 2 and the mould 13 via an injection channel 16. The molten polyurethane deforms the elongate conduit 2 by pressing it into the helical channel 11 on the mandrel 10, so giving rise to the internal helical fin 6. This molten polyurethane hardens to form the corresponding external deformation helix 9. The molten polyurethane also flows into the ring-shaped channel 15 of the cylinder surrounding the conduit 2, so forming the palpable ring 8. The application of heat and pressure (100 Psi and 190° C.) during the injection step sinter the polyurethane onto the elongate conduit 2. In an alternative embodiment the palpable ring 8 is manufactured separately from the conduit 2 and is attached to the exterior of the conduit 2 by means such as clamping.

Figure 2:
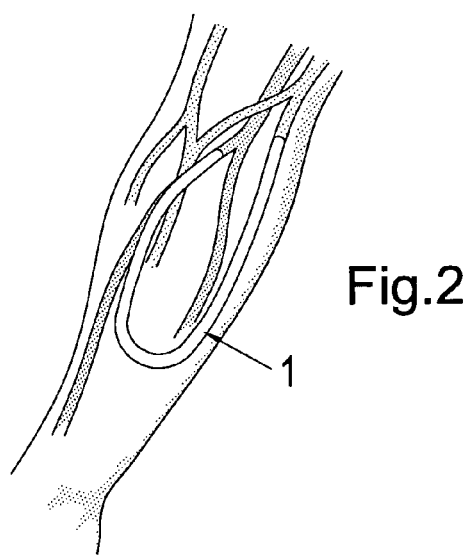
FIG. 2 is a perspective view of a vascular access graft, in accordance with one embodiment of the invention, after implantation in the forearm of a patient, with some hidden details shown.

In use, the vascular access graft 1 is implanted into the forearm or upper thigh of a patient requiring blood dialysis, as is known in the art. As is shown in FIG. 2, the vascular access graft 1 is formed into a U-shape such that the proximal and distal ends 3, 4 are adjacent each other. The proximal end 3 of the vascular graft 1 is sutured to an artery and the distal end 4 of the vascular graft 1 is sutured to a vein such that the artery and the vein are bridged.

Thus, once the vascular access graft 1 is implanted, blood flows from the proximal end 3, through the lumen of the vascular access graft 1, to the distal end 4 of the vascular access graft 1. As the blood passes the internal helical fin 6, helical flow is imparted on the blood which reduces turbulence in the blood, thus reducing the incidence of narrowing of the lumen at the graft/vein junction. Dialysis needles are periodically inserted into the vascular access graft 1, in order to facilitate dialysis of the patient. While a needle is inserted into the access graft, the turbulence of the blood caused by the needle is minimised as the blood passes the internal helical fin 6 and helical flow is imparted on the blood. The helical blood flow pattern imparted by the vascular access graft 1, as is shown in FIG. 7, is also maintained when the needle is inserted in the graft 1. That is, as shown in Example 2, (in particular by the 48 hour and 14 day flow pump analysis results) the helical flow imparted by the helical fin 6 is maintained at increased blood flow rates. Increased blood flow rates occur, e.g. in haemodialysis, due to blood being removed and returned through a needle. Imparting helical flow to the blood flowing through the graft 1 at an increased blood flow rate reduces the turbulent blood flow through the distal anastomosis, thereby reducing the stimulus for tissue build up and/or clotting and possible occlusion of the vascular access graft 1. Furthermore, whilst narrowing of the lumen of the elongate conduit 2 is generally avoided, if such narrowing does occur then blood flow through the elongate conduit 2 is more efficient due to being helical and thus the functional life of the vascular access graft 1 is extended. This, in turn, reduces the number of surgical interventions required to create new dialysis access points for the life time of the patient.

In use, the palpable ring 8 shown in FIG. 3 can be felt through the skin of the patient once the vascular access graft 1 has been implanted. The palpable ring 8 is indicative of the position of the termination point 7 of the helical fin 6 between the proximal and distal ends 3, 4, of the elongate conduit 2. The proximal and distal ends 3, 4 of the conduit 2 can also be felt after implantation at the respective points where they join the appropriate blood vessel of the patient. The length of the conduit 2 bearing the helical fin 6 can be identified as the part of the conduit 2 extending between the distal end 4 of the conduit 2 and the palpable ring 8. It is preferable during dialysis that a needle is not inserted into the length of the conduit 2 bearing the helical fin 6, so as to optimise the helical flow imparted on the blood flowing past the fin 6 and prevent the helical fin 6 obstructing the needle. The presence of the palpable ring 8 enables the needle to be targeted to the access graft 1 between the position of termination point 7 of the helical fin 6 and the proximal end 3 of the elongate conduit 2, so avoiding insertion into the portion of the elongate conduit 2 which bears the helical fin 6.

Vascular access grafts 1 herein described are suitable for implantation anywhere in the body where it is necessary to maintain helical blood flow at increased flow rates. For example, the vascular access graft 1 is for use as a shunt for dialysis in the forearm or leg, as an intravenous line for feeding or drug infusion, or as an access catheter.

Example 1

Introduction

Short flow tests of a 100 mm long straight graft were carried out and confirm that only a single revolution of an internal helical fin in a graft is required in order to impart helical flow on liquid flowing through the graft.

Aim:
To take ultrasound measurements upstream and downstream of a test graft to determine the swirl number (peak transverse velocity versus linear velocity maximum) and the presence of C.T.F.S. (Characteristics Transverse Flow Signature) downstream from a 100 mm long straight graft with and without spiral inserts upstream from the grafts.

Objective:
To compare this 100 mm straight graft with 100 mm spiral grafts and with C.F.D. (Computational Fluid Dynamics) results.

Equipment:
Networked computer equipment (TCT computer and accessories)
Ultrasound equipment (GE LOGIQ 400 CL with Sony camera and accessories)
Flow pump and water bath equipment (Braveheart)

Grafts:
1×100 mm length, no internal fin
1×100 mm length with an internal helical fin having an 8° helix angle and forming approx. 83% of a complete revolution
1×100 mm length with an internal helical fin having a 17° helix angle and forming approx. 83% of a complete revolution.

Spiral Inserts
1. Spiral Insert A
   Description: no fins, 100 mm effective length, latex coated fabric material, 8 mm diameter.
2. Spiral Insert B
   Description: 21 deg fin angle, 2.5 mm fin depth, p3 profile, 1, fin, 60 mm effective length (linear fin length), aluminium material, 8 mm diameter, followed by, no fins, 100 mm effective length, latex coated fabric material, 8 mm diameter.
3. Spiral Insert C
   Description: −21 deg fin angle, 2.5 mm fin depth, p3 profile, 1 fin, 60 mm effective length (linear fin length), aluminium material, 8 mm diameter, followed by, no fins, 100 mm effective length, latex coated fabric material, 8 mm diameter.

Environmental Conditions: Standard room temperature and pressure.

Pump Set Up: CONSTANT 17 mL/s: constant flow of 17 mL/s.

References
Kang and Bonneau 2003, and Cooney 1976 in Biomedical Engineering Principles.

The swirl numbers (peak transverse velocity versus linear velocity maximum) are given in Table 1.

TABLE 1

| Spiral Insert C | −0.002 |
| Spiral Insert A | 0.011 +/−0.009 |
| Spiral Insert B | 0.039 +/− 0.016 |

Observations of the presence or absence of C.T.F.S. (Characteristic Transverse Flow Signature) are given in Table 2.

TABLE 2

| | Control graft | 8 deg graft | 17 deg graft |
| --- | --- | --- | --- |
| −21 deg insert | No C.T.F.S. | No. C.T.F.S. | No. C.T.F.S. |
| No insert | No. C.T.F.S. | C.T.F.S. | C.T.F.S. |
| 21 deg insert | Undetermined | Undetermined | C.T.F.S. |

Conclusion:
C.T.F.S. (Characteristic Transverse Flow Signature), that is to say, coherent flow was observed downstream from the spiral grafts with and without the 21 deg insert. This indicates that a single revolution of the internal helix fin of a graft is capable of conferring helical flow of fluid passing through the graft.

Example 2

A study was conducted to compare the TFT SLF™ Arteriovenous Graft with a non spiral Arteriovenous Graft (control graft) supplied by Vascutek, when implanted as an arteriovenous conduit for hemodialysis access in a pig model.

The primary objective of the study was to determine whether the spiral (TFT) graft performed as intended (i.e. restores spiral laminar blood flow as demonstrated using Doppler Ultra Sound).

Other study targets were to ascertain if spiral flow grafts can be implanted easily and safely in the internal jugular vein and carotid artery; and to study the flow rate and the tendency of the flow pattern during haemodialysis needle cannulation and during the study.

The study was carried out at the University Medical Center Utrecht, Heidelberglaan 100, 3584 CX Utrecht, The Netherlands. All experiments were performed under guidance of qualified BioSurgical personnel following standard operating procedures available at the test facility.

Test Devices:

The spiral flow and straight non spiral flow grafts were individually packaged and identified by a unique serial number (listed below in section 5 of this example).

Overview:

The study used four pigs in total. Two pigs received both the straight and spiral flow graft (uni-versus contralateral) during the same operation and were terminated after 48 hours. Another two animals were treated in the same fashion and were terminated after two weeks. No animals died within 48 hours of surgery.

Animal survival was programmed at two days and two weeks. This documented the presence or absence of thrombus, adequacy of graft function and, intimal hyperplasia. The function of the grafts was assessed by Duplex, and the graft conditions of the 2 weeks survivors were evaluated by explant pathology.

Specific study endpoints were examined and include surgical handling characteristics, in-vivo functioning of the graft, macroscopic and pathological analysis of the device at the conclusion of the study, and morbidity and mortality of the study animals.

Model:

The pigs were of no less than 50 kilograms of weight. The pig model was selected for this study due to their wide use in vascular (surgical) research because of their anatomical and physiological similarity to humans. In addition, pigs were readily available and their size permits various vascular surgical interventions.

Housing and Care:

The animals were acquired from Utrecht University approved vendors approximately two weeks prior to the date of first surgery. Upon arrival at the Animal Laboratory Facility, verification of the test articles was performed and the animals were observed for any adverse physical condition. Test articles will be stored under appropriate conditions.

BioSurgical personnel distinguished the individual animals throughout the study by attaching large easily legible ear tags with unique identification numbers.

The pigs were housed in indoor stalls under standardized conditions, and were provided with food and water twice daily.

Preoperative Medication:

A dose of 80 mg of aspirin was administered orally (PO) to each animal 6 days prior to the surgery. Clopidogrel (Plavix) 225 mg was given 1 day before the operation and was continued until termination. Throughout the study, the dose of Plavix was maintained at 75 mg/d, along with 80 mg/d of aspirin. The animal was heparinized prior to crossclamping.

Animal Preparation and Anaesthesia:

Solid food was removed at least 12 hours preoperatively, with water given ad libitum. The animals were premedicated with azaperon (2.0 mg/kg) and ketamine (1.5 mg/kg), administered by intramuscular injection. An intravenous line was established and each animal received intravenous thiopental (2.0 mg/kg) and atropine (1.0 mg). The animals were endotracheally intubated and mechanically ventilated. Anaesthesia was maintained by supplying a mixture of oxygen and air (1:1 vol/vol), and intravenous infusion of midazolam (0.6 microgram/kg per hour) and sufentanil citrate (0.6 microgram/kg per hour) and pancuronium (Pavulon). All ventilation parameters were adjusted to keep the arterial blood gasses and pH within the physiological range. A rectal temperature probe was placed to record core body temperature.

Surgical Technique:

Through a longitudinal incision in the midline of the neck, the common carotid artery and the internal jugular vein were dissected bilaterally.

Diluted (1:2) papaverine 5 mg/ml was randomly applied locally to prevent vascular spasm.

Baseline flow through the carotid artery and the jugular vein was measured using a 4 mm perivascular flow probe (Transonic Systems).

Heparin 100 IU/kg IV was provided before manipulation of the vessels.

The artery was clamped using atraumatic clamps, and an 8-mm arteriotomy was performed.

An end-to-side anastomosis was created at a 20° to 30° angle using a continuous suture of 8-0 polypropylene.

The ePTFE grafts used measured 6 mm in diameter and 10-15 cm in length. The venous anastomosis was created in a similar fashion.

The blood flow through the artery (i.e., proximal and distal of the anastomosis) and vein (i.e., proximal and distal) was measured several minutes after completing the anastomosis. Graft flow was calculated as flow of the proximal carotid artery minus the flow of the distal artery.

Postoperative Care:

The animals were weaned from the ventilator as soon as there was spontaneous respiration with adequate tidal volumes.

The animals were housed in indoor stalls individually, and were carefully observed.

The animals received analgetics (Buprenorfine, Temgesic, 0.3 mg intramuscular) for the first two days (twice daily), and antibiotics (Clamoxyl) once every two days during 5 days. The animals received 325 mg daily dose of aspirin PO with food for the duration of the study and 75 mg Plavix (PO) daily. Any complications or changes in the animal's condition were immediately reported to the study director. No complications encountered during this study.

Explant Procedures:

The animals were sacrificed at 48 hours (2 animals) and at 14 days (2 animals) respectively. The animals were prepared and anesthetized as described above in the protocol. After the animals were heparinized (100 units/kg), the spiral and straight ePTFE graft patency and competence was assessed by means of angiography and colour doppler ultrasound. While anesthetized, the animals were euthanized with an overdose of barbiturate/saturated KCL solution intravenously.

Histopathology:

Upon study termination vein and artery were perfused with buffer solution and the segments with the prosthesis were explanted, preserved in provided sample containers and transported to the pathology lab.

Veterinary Supervision:

All experiments were performed under guidance of qualified BioSurgical personnel following standard operating procedures available at the test facility. On a daily basis the health of the animals was assessed by the attending veterinary and no health issues were observed.

Test Article Identification, Study Dates and Duration Devices Used

| Device Type | Numbers |
| --- | --- |
| Spiral Graft | S1 to S4 |
| Control Graft | C1 to C4 |

Device ID, Study Dates and Implant Duration

| Animal Number | Device Number & Type | Implant Date | Explant Date | Implant Duration |
|---|---|---|---|---|
| 1 | S1 | 08 Sep. 2009 | 10 Sep. 2009 | 48 Hours |
| 1 | C1 | 08 Sep. 2009 | 10 Sep. 2009 | 48 Hours |
| 2 | S2 | 08 Sep. 2009 | 10 Sep. 2009 | 48 Hours |
| 2 | C2 | 08 Sep. 2009 | 10 Sep. 2009 | 48 Hours |
| 3 | S3 | 10 Sep. 2009 | 24 Sep. 2009 | 14 days |
| 3 | C3 | 10 Sep. 2009 | 24 Sep. 2009 | 14 days |
| 4 | S4 | 10 Sep. 2009 | 24 Sep. 2009 | 14 days |
| 4 | C4 | 10 Sep. 2009 | 24 Sep. 2009 | 14 days |

Detailed Examination of the Spiral Flow Graft and Control Grafts Results
Inspection—Angiography and Peri-Operative Findings
48 Hour Explant Angiography:

Both Pig 1 and pig 2 showed patent carotid, access grafts (both Spiral and Control grafts).

Pig 1 had normal patency of jugular veins while pig 2 had limited narrowing/spasm in the distal jugular vein, distal to the venous anastomosis.
Peroperative Findings at 48 Hour Explant After exposure of the surgical site, dissection of the grafts showed satisfactory early surgical changes, no complication, intact anastomoses in both pig 1 and 2.
14 Day Explant Angiography:

Both Pig 3 and pig 4 showed patent carotid, access grafts (both Spiral and Control grafts). Pig 4 had narrowing/spasm in the proximal anastamosis and had normal patency of jugular veins while pig 3 had limited narrowing/spasm up to maximum half the diameter of the outflow part on the venous side (distal jugular vein, distal to the venous anastomosis).
Peroperative Findings at 14 Day Explant After exposure of the surgical site, dissection of the grafts showed satisfactory early surgical changes, no complication, intact anastomoses in both pig 3 and 4.
Histological Data
48 Hour Macroscopic Findings At explant, the graft and distal anastomoses were excised and examined by longitudinal section. The interior of the spiral grafts was examined and photographed.

There was no evidence of thrombus within the spiral graft, around the ridges and in particular no adverse finding at the distal anastomosis.
Colour Doppler Ultrasound Results
Peroperative Colour Doppler Ultrasound
48 Hour Explants
Pig 1:

The spiral and control grafts were widely patent with widely patent anastamoses. The venous anastamoses peak systolic velocities were 160 mls/sec spiral graft and 244 cm/sec for control.

Initial assessment of the spiral graft distal anastomosis showed a spiral flow pattern with a superimposed recirculation most marked in diastole. No spiral flow was seen in the control graft, distal anastomosis or distal jugular vein. In particular a double helix, in keeping with non-spiral flow was seen at the distal anastamosis.

As a second step in intra-operative monitoring, it was decided to ligate the jugular vein proximal to the distal anastamosis as a component of jugular non-spiral flow arising proximally in the jugular vein may contribute to this.
AFTER Proximal Jugular Vein Ligation:

Spiral flow was demonstrated at the distal anastamosis and distal to the distal anastamosis in the spiral graft. No spiral flow was seen in the distal anastamosis or vein in the control graft. The obtained effect of ligation was to improve the spiral flow seen in the spiral graft, and this effect was indeed clearly observed.
Pig 2:

The spiral and control grafts were widely patent with widely patent anastamoses. The venous anastamoses peak systolic velocities were similar 150-180 cm/sec.

The distal jugular vein on the spiral graft was noted to be reduced calibre. Ligation of the proximal jugular vein was performed and demonstrated improved spiral flow at the distal anastamosis in the spiral graft.
14 Day Explants
Pig 3:

The spiral and control grafts were widely patent with widely patent anastamoses. The venous anastamoses peak systolic velocities were 146 cm/sec spiral graft and 403 cm/sec for control.

Initial assessment of the spiral graft distal anastomosis showed a spiral flow pattern.

No spiral flow was seen in the control graft, distal anastomosis or distal jugular vein. In particular a double helix, in keeping with non-spiral flow was seen at the distal anastomosis. The ligation of the proximal internal jugular vein was not possible as access at 14 days implant was too scarred: to ligate would have risked the whole graft occluding prior to the flow assessments. This did not adversely affect the trial—in fact the combination of ligated and nonligation of internal jugular and flow assessments gave greater value to the results as more robust spiral flow induction i.e. Independent of outflow configuration.
Pig 4:

The spiral and control grafts were widely patent with widely patent anastamoses. The venous anastamoses peak systolic velocities were 244 cm/sec spiral graft and 178 cm/sec for control. It was noted that the ingraft peak systolic velocity for the control graft was low at 44 cm/sec.

Initial assessment of the spiral graft distal anastomosis showed a spiral flow pattern. No spiral flow was seen in the control graft, distal anastomosis or distal jugular vein.
48 Hour Flow Probe Analysis:

The flow through the carotid proximal to the spiral graft were measured at explant. The results were 570 mls/min for both pigs.
14 Day Flow Probe Analysis:

The flow through the distal jugular vein, distal to the spiral grafts were measured at explant. The results were 1340, and 330 mls/min for both pigs.
48 Hour Flow Pump Analysis:

Venous Cannula was placed in the spiral graft within 1.5 cm from the junction of the spiral segment and nonspiral graft segment, with the cannula pointing in the direction of flow. The arterial (inflow) cannula was placed in the carotid artery ipsilateral to the spiral graft venous anastomosis. This was done with the cannula pointing retrogradely in the carotid artery. The flow probe was placed distal to the carotid artery cannula but proximal to the other graft arterial anastomosis. This was designed to test the increased flow rate through the graft, graft and anastomosis integrity and the effect of increased flow rate on the distal anastomosis flow pattern i.e. maintenance of spiral flow.

The flow pump was set at 30%, then reduced at 10% intervals to zero, then retested at 30% or 40%. From previous experiments the flow rate for the % was assessed as:

| | |
|---|---|
| 10% | 160 mls/min |
| 20% | 240 mls/min |
| 30% | 420 mls/min |
| 40% | 490 mls/min |
| 50% | 570 mls/min |
| 60% | 660 mls/min |

For Pig 1, the spiral flow pattern was seen to be maintained from 0 to 40%.

For Pig 2, the spiral flow pattern was seen to 20% but a double helix indicating loss of spiral flow was seen at 30 and 40%. This indicated that in this spiral implant the spiral flow was induced up to 240 mls/min i.e in excess of basal flow rate. This had no adverse effect on the trial.

14 Day Flow Pump Analysis:

Venous Cannula was placed in the spiral graft at the junction of the spiral segment and nonspiral graft segment, with the cannula pointing in the direction of flow. The arterial (inflow) cannula was placed in the carotid artery ipsilateral to the spiral graft venous anastomosis. This was done with the cannula pointing retrogradely in the carotid artery. The flow probe was placed distal to the graft venous anastomosis. This was designed to test the increased flow rate through the graft, graft and anastomosis integrity and the effect of increased flow rate on the distal anastomosis flow pattern i.e. maintenance of spiral flow.

The flow pump was set at 10%, then increased at 10% intervals to 40/50%, then reduced in 10% increments back to or 0%. From previous experiments the flow rate for the % was assessed as:

| | |
|---|---|
| 10% | 160 mls/min |
| 20% | 240 mls/min |
| 30% | 420 mls/min |
| 40% | 490 mls/min |
| 50% | 570 mls/min |
| 60% | 660 mls/min |

Pig 3:

The insertion point of the needle was antegrade such that tip of needle was within spiral segment and close to anastamosis. This relative less efficiency in inducing spiral flow would be expected and supports the IFU that state needle puncture should not be in the spiral segment of the graft. No adverse effect on graft however, so no adverse effect on trial Pig 4:

The spiral flow was seen at 0-50% and then back to 0%. The needle puncture site was noted to be 1.5 cm proximal to the spiral ridge, i.e. 50 mm proximal to distal anastomosis.

Summary of Results:

Four pigs in total. Two pigs received both the straight and spiral flow graft (uni-versus contralateral) during the same operation and were terminated after 48 hours. Another two animals were treated in the same fashion and were terminated after two weeks.

Animal survival was programmed at two days and two weeks. This documented the presence or absence of thrombus, adequacy of graft function and, intimal hyperplasia At explant, the graft and distal anastomoses were excised and examined by longitudinal section. There was no evidence of thrombus within the spiral graft, around the ridges and in particular no adverse finding at the distal anastomosis.

Spiral flow was demonstrated at the distal anastomosis and distal to the distal anastomosis in the spiral graft. No spiral flow was seen in the distal anastomosis or vein in the control graft. The obtained effect of ligation was to improve the spiral flow seen in the spiral graft, and this effect was indeed clearly observed.

The spiral flow induction was maintained if the flow rate was increased by dialysis cannulae in situ in the spiral graft and pump. The approximate increase in flow that led to maintained spiral flow through the distal anastamosis in the spiral grafts was in the range of 240 mls/min to 570 mls/min.

Conclusion:

The key findings of this study at 48 hours and 14 days are:

This model appears robust, and performed with high expertise and satisfactory outcome for detailed flow analysis of grafts.

The Spiral Access Graft induces spiral flow through venous anastamosis, whereas the Control graft does not.

The ligation of the ipsi-lateral jugular vein proximal to the distal anastomosis allowed assessment of a unidirectional outflow and a bidirectional outflow model. The ligation of this vein produced data from a unidirectional outflow at 48 hours, whereas the unligated model produces a bidirectional model at 14 days.

This may be of benefit as both models showed spiral flow outflow in the spiral access graft anastanosis.

The spiral flow induction is maintained if the flow rate is increased by dialysis cannulae and pump.

Macroscopic assessment of the spiral grafts at explant showed no evidence of thrombosis, vessel wall trauma or distal thrombosis.

There were no adverse events observed during the study.

What is claimed is:

1. A vascular access graft comprising:
   an elongate conduit having distal and proximal ends and a length therebetween, an inner surface, an exterior and longitudinal axis, at least a portion of the elongate conduit having a self-sealing property such that the portion remains impermeable after puncturing by a dialysis needle; and
   a helical fin projecting inwardly from the inner surface of the elongate conduit, having a first and a second end and a length therebetween, and extending parallel to the longitudinal axis of the elongate conduit, wherein the helical fin extends from the distal end of the elongate conduit to a termination point which is short of the proximal end of the elongate conduit; and
   an external palpable protrusion positioned on the exterior of the elongate conduit, wherein the positioning of the protrusion on the elongate conduit corresponds to the position of the termination point of the helical fin between the distal and proximal ends of the elongate conduit.

2. A vascular access graft comprising:
   an elongate conduit having distal and proximal ends and a length therebetween, an inner surface, an exterior and longitudinal axis, at least a portion of the elongate conduit having a self-sealing property such that the portion remains impermeable after puncturing by a dialysis needle;
   a helical fin projecting inwardly from the inner surface of the elongate conduit, having a first and a second end and a length therebetween, and extending parallel to the longitudinal axis of the elongate conduit,
   wherein the helical fin consists of between 80% and 120% of one single revolution,
   wherein the helical fin extends from the distal end of the elongate conduit to a termination point which is short of the proximal end of the elongate conduit; and an external palpable protrusion positioned on the exterior of the elongate conduit, wherein the positioning of the protrusion on the elongate conduit corresponds to the position of the termination point of the helical fin between the distal and proximal ends of the elongate conduit.

3. The vascular access graft according to claim 1 wherein the helical fin has a helix angle of between 5° and 20°.

4. The vascular access graft according to claim 3 wherein the helix angle of the helical fin changes over the length of the helical fin.

5. The vascular access graft according to claim 1 wherein the helical fin consists of between 50% and 150% of one single revolution.

6. The vascular access graft according to claim 2 wherein the external palpable protrusion is a palpable ring which completely or partially encircles the exterior of the elongate conduit.

7. The vascular access graft according to claim 2 wherein the external palpable protrusion extends between 1 mm and 4 mm from the exterior of the elongate conduit.

8. The vascular access graft according to claim 2 wherein the external palpable protrusion has a length of between 3 mm and 6 mm along the length of the elongate conduit.

9. The vascular access graft according to claim 1 further comprising an external helical formation extending axially around the exterior of the elongate conduit, for supporting the elongate conduit.

10. The vascular access graft according to claim 9 wherein the helix angle of the external helical formation is greater than the helix angle of the helical fin.

11. The vascular access graft according to claim 9 wherein the external helical formation has a helix angle of greater than 50°.

12. The vascular access graft according to claim 2 further comprising an axially extending external deformation helix located around the exterior of the elongate conduit, wherein the axially extending external deformation helix deforms the elongate conduit so as to provide the helical fin projecting inwardly from the inner surface of the elongate conduit, such that the helical fin corresponds to the axially extending external deformation helix, and wherein the external palpable protrusion is an integral part of the deformation helix.

13. The vascular access graft according to claim 12 wherein the elongate conduit is made from ePTFE, and the axially extending external deformation helix and external palpable protrusion are made from polyurethane.

14. The vascular access graft according to claim 2 wherein the helical fin extends from the distal end of the elongate conduit for less than 25% of the total length of the elongate conduit.

15. The vascular access graft according to claim 2 wherein the helical fin extends from the distal end of the elongate conduit for less than 15% of the total length of the elongate conduit.

16. The vascular access graft according to claim 1 wherein the helical fin has a helix angle of between 8° and 16°.

17. The vascular access graft according to claim 1 wherein the helical fin consists of between 80% and 120% of one single revolution.

18. The vascular access graft according to claim 2 wherein the external palpable protrusion extends 2 mm from the exterior of the elongate conduit.

19. The vascular access graft according to claim 2 wherein the helical fin extends from the distal end of the elongate conduit for less than 50% of the total length of the elongate conduit.

* * * * *